US00PP18368P2

(12) United States Plant Patent
Watson

(10) Patent No.: US PP18,368 P2
(45) Date of Patent: Dec. 25, 2007

(54) ***DAPHNE* PLANT NAMED 'HEWREB'**

(50) Latin Name: *Daphne adora*
Varietal Denomination: HEWREB

(76) Inventor: Steven Watson, 2 Bedford Park, Bere Alston, Yelverton, Devon (GB), PL20 7DQ ( * ) Notice: Subject to any disclaimer, the term of this patent is extended or adjusted under 35 U.S.C. 154(b) by 130 days.

(21) Appl. No.: 11/352,970

(22) Filed: Feb. 13, 2006

(51) Int. Cl.
*A01H 5/00* (2006.01)

(52) U.S. Cl. ..... Plt./226

(58) Field of Classification Search ..... Plt./226
See application file for complete search history.

*Primary Examiner*—Howard J. Locker

(57) ABSTRACT

A new cultivar of *Daphne* plant named 'HEWREB' that is characterized by moderately dense habit, variegated dark green leaves with a broad yellow margin, and fragrant pale purple flowers. In combination these traits set 'HEWREB' apart from all other existing varieties of *Daphne* known to the inventor.

2 Drawing Sheets

Genus: *Daphne*. Species: *odora*.
Denomination: 'HEWREB'.

BACKGROUND OF THE INVENTION

The present invention relates to a new and distinct cultivar of *Daphne* grown as an ornamental plant for use in the landscape. The new cultivar is known botanically as *Daphne odora* and will be referred to hereinafter by the cultivar name 'HEWREB'.

'HEWREB' was discovered by the inventor in 1989 as a single variegated branch sport on an individual *Daphne odora* 'Aureomarginata' (unpatented). The inventor selected 'HEWREB' from an individual plant of *Daphne odora* 'Aureomarginata'. The parent plant is *Daphne odora* 'Aureomarginata'. 'HEWREB' is distinguishable from 'Aureomarginata' is *Daphne odora* 'Aureomarginata'. 'HEWREB' is distinguishable from 'Aureomarginata' by a much broader yellow marginal band.

'HEWREB' is an ornamental shrub of moderately compact habit and foliage that is dark green with a broad yellow margin and strongly scented pale purple flowers.

The closest comparison plant known by the inventor is the parent plant *Daphne odora* 'Aureomarginata'. 'HEWREB' is most readily distinguished from its parent, 'Aureomarginata' by its wider yellow margin.

'HEWREB' was first asexually propagated in 1993 by the inventor in Devon, England. Asexual propagation was accomplished using semi-hardwood cuttings. Since that time, under careful observation, the distinguishing characteristics of 'HEWREB' have been determined stable and uniform, and are reproduced true to type in successive generations of asexual reproduction.

An application for a grant of European Community Plant Breeders Rights was filed on Jan. 21, 2005, serial number 2005/0104. No plants of 'HEWREB' have been made available to the public prior to the date of filing of the instant plant patent application.

SUMMARY OF THE INVENTION

The following represent the distinguishing characteristics of the new *Daphne odora* cultivar 'HEWREB'. In combination these traits set 'HEWREB' apart from all other existing varieties of *Daphne* known to the inventor. 'HEWREB' has not been tested under all possible conditions and phenotypic differences may be observed with variations in environmental, climatic, and cultural conditions, however, without any variance in genotype.

1. *Daphne odora* 'HEWREB' exhibits variegated foliage.
2. *Daphne odora* 'HEWREB' has dark green leaves with a wide yellow margin.
3. *Daphne odora* 'HEWREB' is 1.3 m in height and 1.3 m width at maturity.
4. *Daphne odora* 'HEWREB' exhibits fragrant pale purple flowers that bloom from mid-winter to early spring.
5. *Daphne odora* 'HEWREB' exhibits moderately compact habit.
6. *Daphne odora* 'HEWREB' is suitable for use as a low accent plant, mass plants in the landscape, and as a container plant.
7. *Daphne odora* 'HEWREB' performs well in well-drained, moist soils.
8. *Daphne odora* 'HEWREB' is hardy to USDA Zone 7.

BRIEF DESCRIPTION OF THE DRAWINGS

The accompanying color drawings illustrate the overall appearance of the new *Daphne* cultivar 'HEWREB' showing the colors as true as it is reasonably possible to obtain in colored reproductions of this type. Colors in the drawings may differ from the color values cited in the detailed botanical description, which accurately describe the actual colors of the new variety 'HEWREB'.

The drawings labeled FIG. 1 and FIG. 2 were taken in the spring of ten year old plants growing out of doors in Essex, England. The plants were not treated with any chemicals.

The drawing labeled

The drawing labeled

Figure 1:
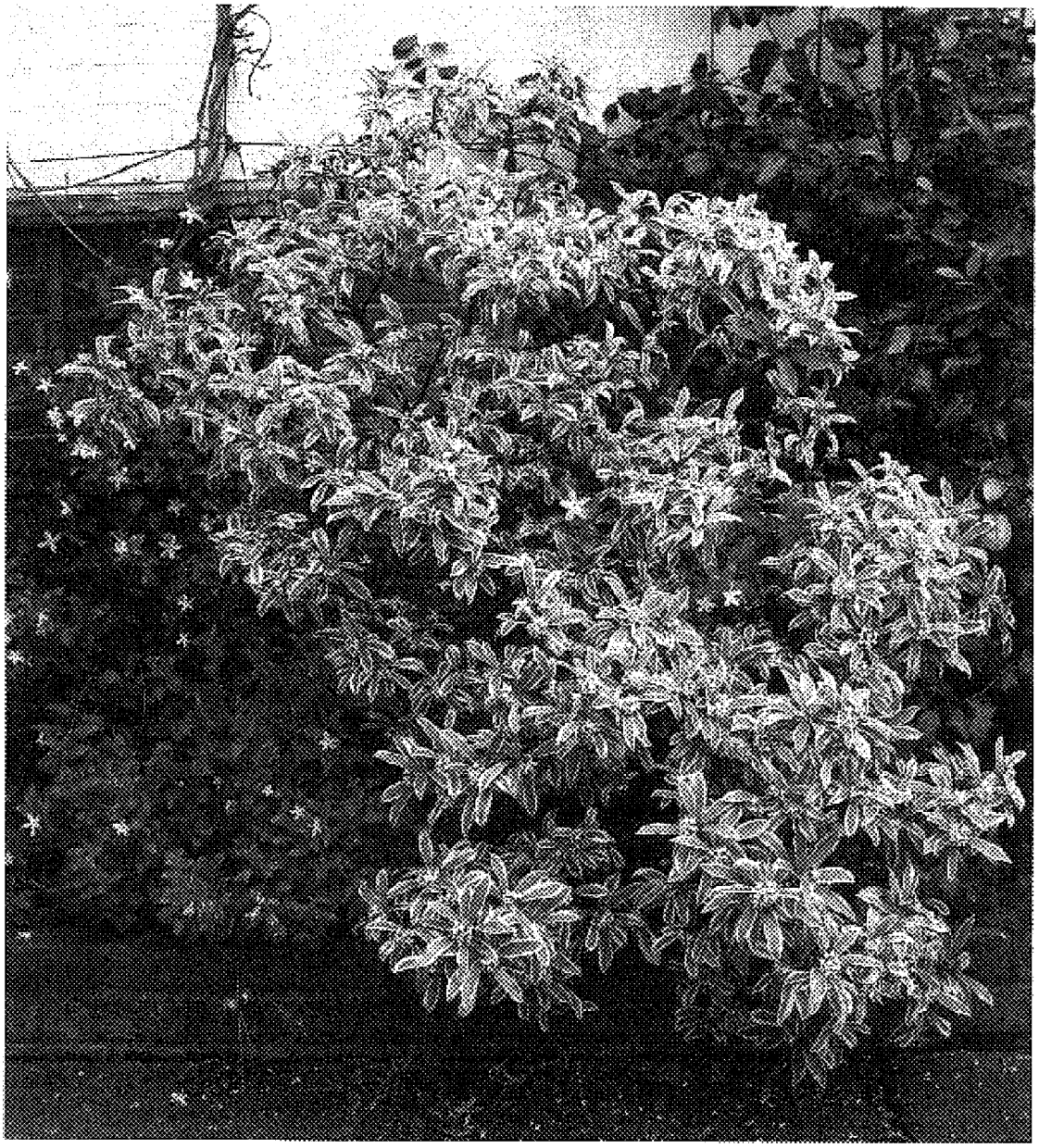
FIG. 1 shows a whole plant in a landscape setting.
Figure 2:
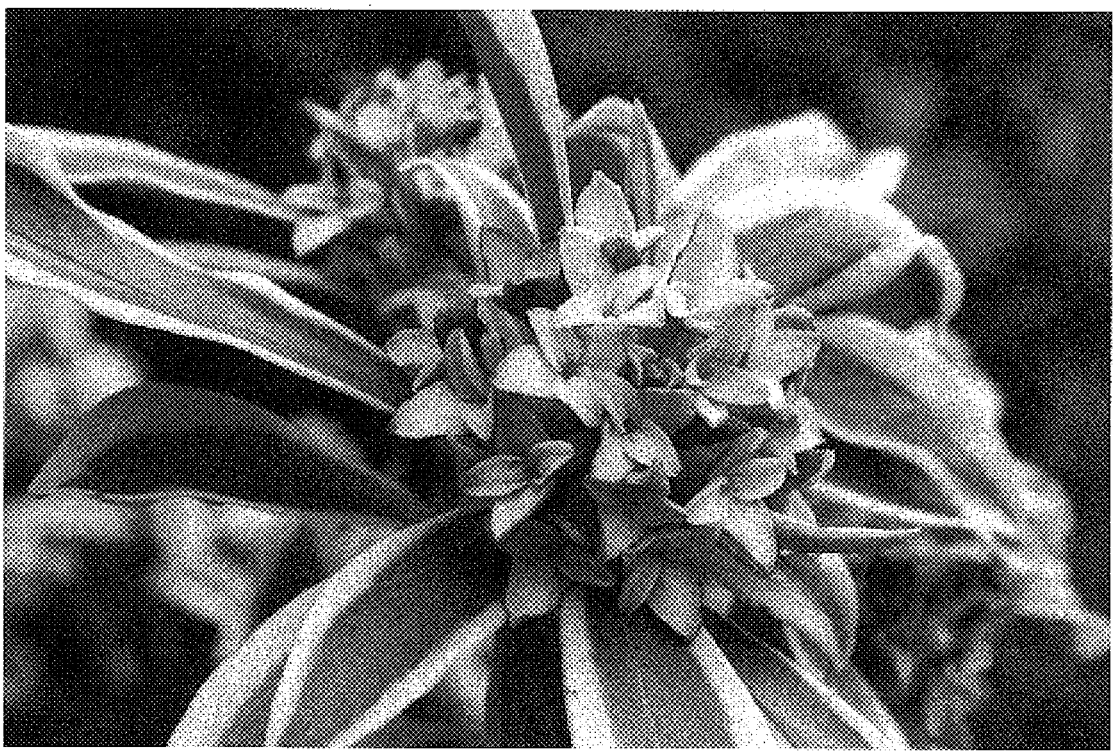
FIG. 2 shows a close up of the flower cluster.

The drawings have been made from photographs taken by conventional techniques and although foliage colors may appear different from actual colors due to light reflectance, they are accurate as possible by conventional photography.

BOTANICAL DESCRIPTION OF THE PLANT

The following is a detailed description of *Daphne odora* cultivar named 'HEWREB'. Data was collected from September 2005 until January 2006 from plants grown out of doors in Essex, England. The plants are approximately 10 years old. Color determinations are in accordance with the 2001 Edition of the Colour Chart of The Royal Horticultural Society, London, England, except where general color terms of ordinary dictionary significance are used. 'HEWREB' has not been tested under all possible conditions and phenotypic differences may be observed with variations in environmental, climatic, and cultural conditions; however, without any variance in genotype. The growing requirements are similar to the species.

Botanical classification: *Daphne odora* 'HEWREB'.
Genus: *Daphne*.
Species: odora.
Denomination 'HEWREB'.
Commercial classification: Ornamental shrub.
Common name: Daphne.
Uses: Border shrub or in containers.
Container size: Suggested container size is 1.5 to 2 liters for producing a one or two year old plant.
Cultural requirements: Plant in good general garden soil not prone to waterlogging; full sun to partial shade.
Parentage: 'HEWREB' was discovered as a single variegated branch sport on an individual *Daphne odora* 'Aureomarginata'.
Plant description:
- *Blooming season.*—From mid-winter into spring.
- *Plant habit.*—Moderately dense.
- *Vigor.*—Moderately vigorous.
- *Plant form.*—Moderately open.
- *Plant dimensions* (*at maturity*).—1.3 m in height, 1.3 m in width.
- *Hardiness.*—Hardy to USDA Zone 7.
- *Propagation.*—Semi-hardwood cuttings.
- *Root system.*—Fleshy.
- *Time to initiate roots.*—12–14 weeks are needed to produce roots on an initial cutting.
- *Air temperature to develop roots on initial cuttings.*—An air temperature of 23° Centigrade is ideal to produce roots on initial cuttings.
- *Crop time.*—10–12 months as a liner; one further growing season to produce a flowering plant in a 1 liter container.
- *Seasonal interest.*—Fragrant pale purple flowers from mid-winter to spring; green leaves with wide yellow margins year round.
- *Diseases and pests.*—No particular susceptibility or resistance to pests or diseases has been observed by the inventor.

Stem:
- *Mature branch color.*—Between 200B and 200C.
- *Mature branch surface.*—Slightly rough.
- *Mature branch lenticels shape.*—Linear-elliptic.
- *Mature branch lenticels color.*—Between N199B and N199C.
- *One year shoot dimensions.*—37 mm in length, 3.5 mm in diameter.
- *Internode length.*—1.75 cm between nodes.
- *Shape.*—Moderately open, usually di- or trichotomous.
- *Stem color.*—Between 146B and 146C where shaded becoming tinged with 178A in direct sunlight.

Foliage:
- *Type.*—Evergreen to semi-deciduous.
- *Internode length.*—8 mm at base to 1 mm at the tip of an individual shoot.
- *Arrangement.*—Alternate; unevenly distributed with most grouped toward tip.
- *Leaf.*—Dimensions: 73 mm in length, 17 mm in width. Color (adaxial): Center 137B, broad, 3 mm to 4 mm wide marginal band of 160B. Color (abaxial): Center 138A, broad, 3 mm to 4 mm wide marginal band of 160B. Texture: Thick and leathery. Division: Entire and unlobed. Shape: Elliptic-obovate. Base: Cuneate. Apex: Mucronate. Margin: Entire. Venation: Pinnate. Vein color (adaxial and abaxial): 147D. Surface (adaxial and abaxial): Smooth. Attachment: Sessile. Foliar fragrance: None observed.

Flower:
- *Inflorescence.*—Terminal heads.
- *Number of flowers in a terminal inflorescence.*—17 to 23.
- *Inflorescence depth.*—15 mm to 20 mm.
- *Inflorescence diameter.*—26 mm to 35 mm.
- *Peduncle.*—None.
- *Bud.*—Shape: Upper third ellipsoid, lower two thirds cylindrical. Dimensions: 12 mm in length, 2 mm in diameter. Color: Upper third (lobes) 59C. Lower two thirds (tube) nearest 176B.
- *Pedicel.*—Dimensions: 2 mm in length, 1 mm in diameter. Color: 139D. Pubescence: Present, fine, white.
- *Flower.*—Dimensions: 13 mm in length, 11 mm in width. Persistent or self-cleaning: Self-cleaning. Type: Single. Fragrance: Very strong and sweet. Shape: Trumpet-shape. Aspect: Tightly congested into inflorescence so aspect dependent on position in inflorescence. Calyx: Dimensions: 11 mm in length. Tube dimensions: 7 mm in length, 2 mm in diameter. Tube pubescence: Absent. Tube color: Between 75B and 75C. Number of lobes: 4 arranged in 2 whorls of 2. Lobe shape: Ovate. Lobe tip shape: Obtuse. Lobe margins: Entire, slightly inrolled. Outer lobe dimensions: 7 mm in length, 4 mm in width. Inner lobe dimensions: 5 mm in length, 3 mm in width. Lobe pubescence: Absent. Outer lobe surface color: Outer lobes, 70B; inner lobes between 75A and 75B. Inner lobe surface color: Outer and inner lobes 76D. Corolla: Absent, as is characteristic of the genus.

Reproductive organs:
- *Stamens.*—Number: 8, mostly imperfect, being reduced to slender white threads approximately 1 mm long. Filament dimensions: Less than 1 mm in length. Filament color: 155C. Anther dimensions: Where apparently complete, less than 1 mm in length and width. Anther color: 16A. Pollen color: None produced.
- *Pistil.*—Number: 1 Stigma shape: Circular, flattened cushion shape. Stigma dimensions: Less than 0.5 mm in length, 1 mm in diameter. Stigma color: 155C, translucent. Style shape: Broad ovoid. Style dimensions: Length and diameter both approximately 0.8 mm. Style color: Nearest 150D.

*Ovary.*—Dimensions: 1.5 mm in length, 1 mm in diameter. Shape: Ellipsoid. Position: Superior. Color: 145B.

Seed: None produced.

It is claimed:

1. A new and distinct cultivar of *Daphne* plant named 'HEWREB' as described and illustrated herein.

* * * * *